(12) United States Patent
Wiek et al.

(10) Patent No.: US 9,017,619 B2
(45) Date of Patent: Apr. 28, 2015

(54) DEVICE AND METHOD FOR DISINFECTING, STERILIZING AND/OR LOOKING AFTER MEDICAL, IN PARTICULAR DENTAL, INSTRUMENTS

(75) Inventors: Hans-Dieter Wiek, Hochdorf (DE); Johann Stempfle, Pfaffenhofen (DE); Herbert Lott, Bad Wurzach (DE); Frank Saur, Ulm (DE)

(73) Assignee: Kaltenbach & Voigt GmbH, Biberach (DE)

(*) Notice: Subject to any disclaimer, the term of this patent is extended or adjusted under 35 U.S.C. 154(b) by 498 days.

(21) Appl. No.: 12/988,777

(22) PCT Filed: Mar. 20, 2009

(86) PCT No.: PCT/EP2009/002079
§ 371 (c)(1),
(2), (4) Date: Jan. 18, 2011

(87) PCT Pub. No.: WO2009/129902
PCT Pub. Date: Oct. 29, 2009

(65) Prior Publication Data
US 2011/0206555 A1    Aug. 25, 2011

(30) Foreign Application Priority Data
Apr. 24, 2008    (DE) .................. 10 2008 020 586

(51) Int. Cl.
| A61L 2/00 | (2006.01) |
| A61L 9/00 | (2006.01) |
| A61L 2/18 | (2006.01) |
| A61L 2/07 | (2006.01) |

(52) U.S. Cl.
CPC .... *A61L 2/18* (2013.01); *A61L 2/07* (2013.01)

(58) Field of Classification Search
CPC ...... B08B 9/032; B08B 3/00; A61L 2202/24; A61L 2/26; A61L 2/07; A61L 2/18
USPC .................. 422/292, 295, 297, 300
See application file for complete search history.

(56) References Cited

U.S. PATENT DOCUMENTS

| 3,769,028 A | * | 10/1973 | Katz et al. ............... 426/232 |
| RE28,524 E | * | 8/1975 | Brebant .................... 202/175 |
| 4,088,444 A | * | 5/1978 | Byrne ....................... 422/25 |
| 4,336,329 A | * | 6/1982 | Hesse et al. .............. 435/3 |

(Continued)

FOREIGN PATENT DOCUMENTS

| DE | 2814147 A1 | 10/1978 |
| DE | 40 24 171 A1 | 2/1992 |

(Continued)

OTHER PUBLICATIONS

U.S. Appl. No. 60/972,034, filed Sep. 13, 2007.*

(Continued)

*Primary Examiner* — Regina M Yoo
(74) *Attorney, Agent, or Firm* — Marshall, Gerstein & Borun LLP

(57) ABSTRACT

Device and method for disinfecting, sterilizing, and/or looking after medical, in particular dental, instruments, comprising a rinsing chamber in which there are holders for receiving the instruments, wherein at least parts of the walls of the rinsing chamber or elements located in the rinsing chamber can be cooled.

15 Claims, 4 Drawing Sheets

(56) References Cited

U.S. PATENT DOCUMENTS

| | | | |
|---|---|---|---|
| 4,576,792 A * | 3/1986 | Martensson | 422/27 |
| 5,197,499 A | 3/1993 | Bodenmiller et al. | |
| 5,533,539 A * | 7/1996 | Sutter et al. | 134/95.2 |
| 5,571,488 A | 11/1996 | Beerstecher et al. | |
| 6,645,430 B1 * | 11/2003 | Lin | 422/28 |
| 2002/0044898 A1 * | 4/2002 | Sergio et al. | 422/300 |
| 2002/0163636 A1 * | 11/2002 | Oberleitner et al. | 356/128 |
| 2003/0190257 A1 * | 10/2003 | Halstead et al. | 422/28 |
| 2004/0091389 A1 | 5/2004 | Malkin et al. | |
| 2006/0151401 A1 * | 7/2006 | Karimnia | 210/758 |
| 2007/0031778 A1 * | 2/2007 | Helfenbein et al. | 433/82 |
| 2007/0224077 A1 * | 9/2007 | Cox et al. | 422/1 |
| 2008/0166264 A1 * | 7/2008 | Halstead et al. | 422/29 |
| 2008/0193337 A1 * | 8/2008 | Ongaro et al. | 422/101 |
| 2009/0000648 A1 * | 1/2009 | Schaffarzick | 134/28 |
| 2009/0071636 A1 * | 3/2009 | Novotny | 165/104.33 |

FOREIGN PATENT DOCUMENTS

| | | | |
|---|---|---|---|
| EP | 0 638 297 A1 | 2/1995 | |
| GB | 1555295 A | 11/1979 | |
| WO | WO-9010464 A1 | 9/1990 | |
| WO | WO-9801386 A2 | 1/1998 | |
| WO | WO-0059553 A1 | 10/2000 | |
| WO | WO 2006126103 A2 * | 11/2006 | A61L 2/07 |

OTHER PUBLICATIONS

International Search Report for PCT/EP2009/002079 dated Jul. 27, 2009.

* cited by examiner

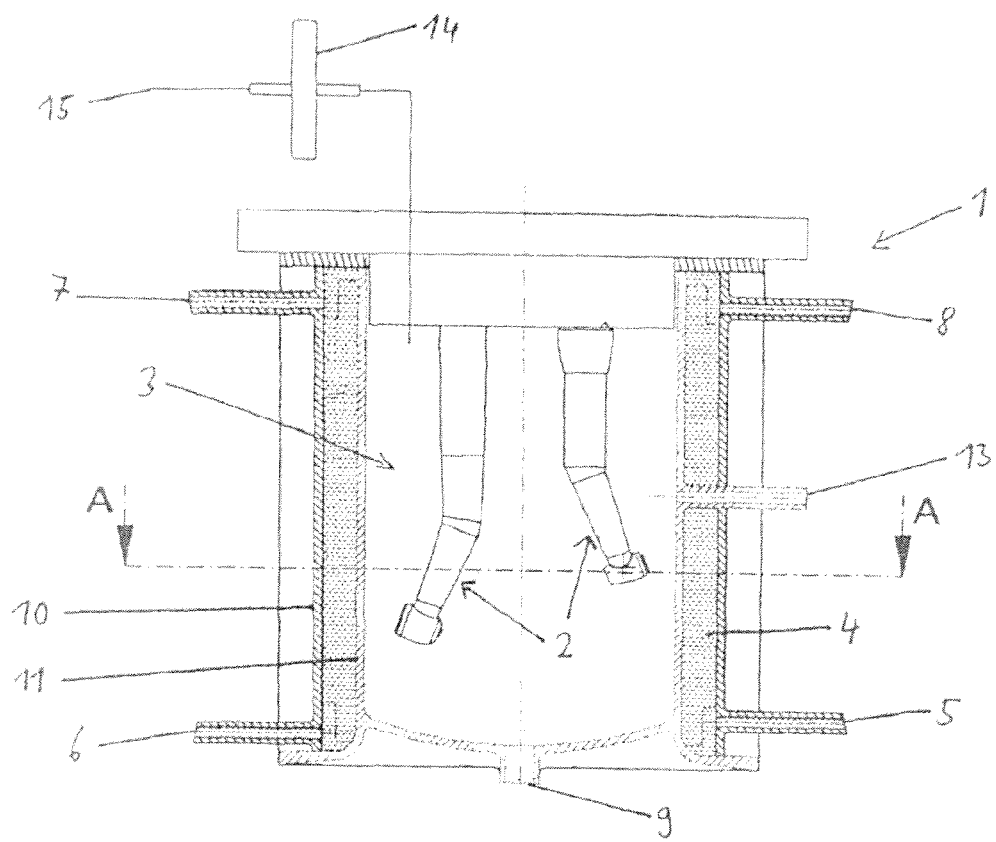
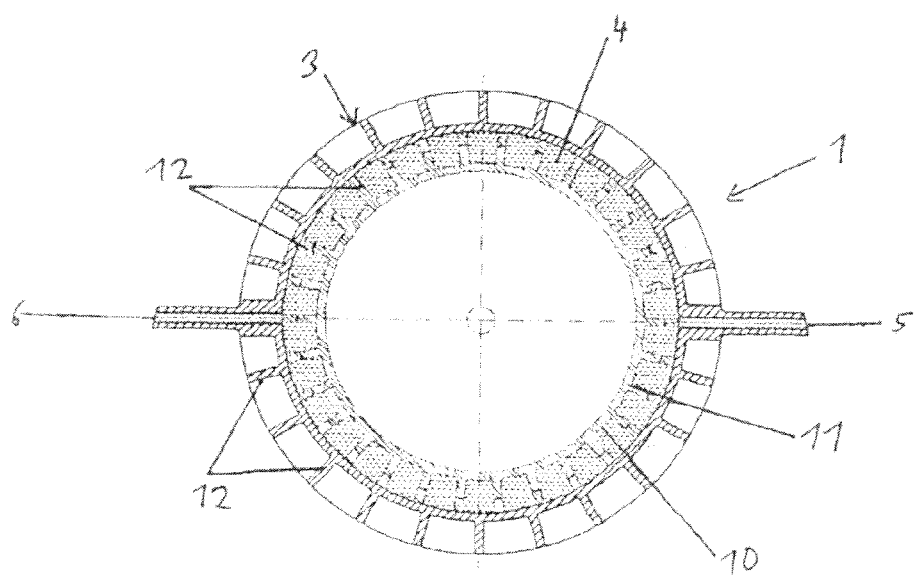

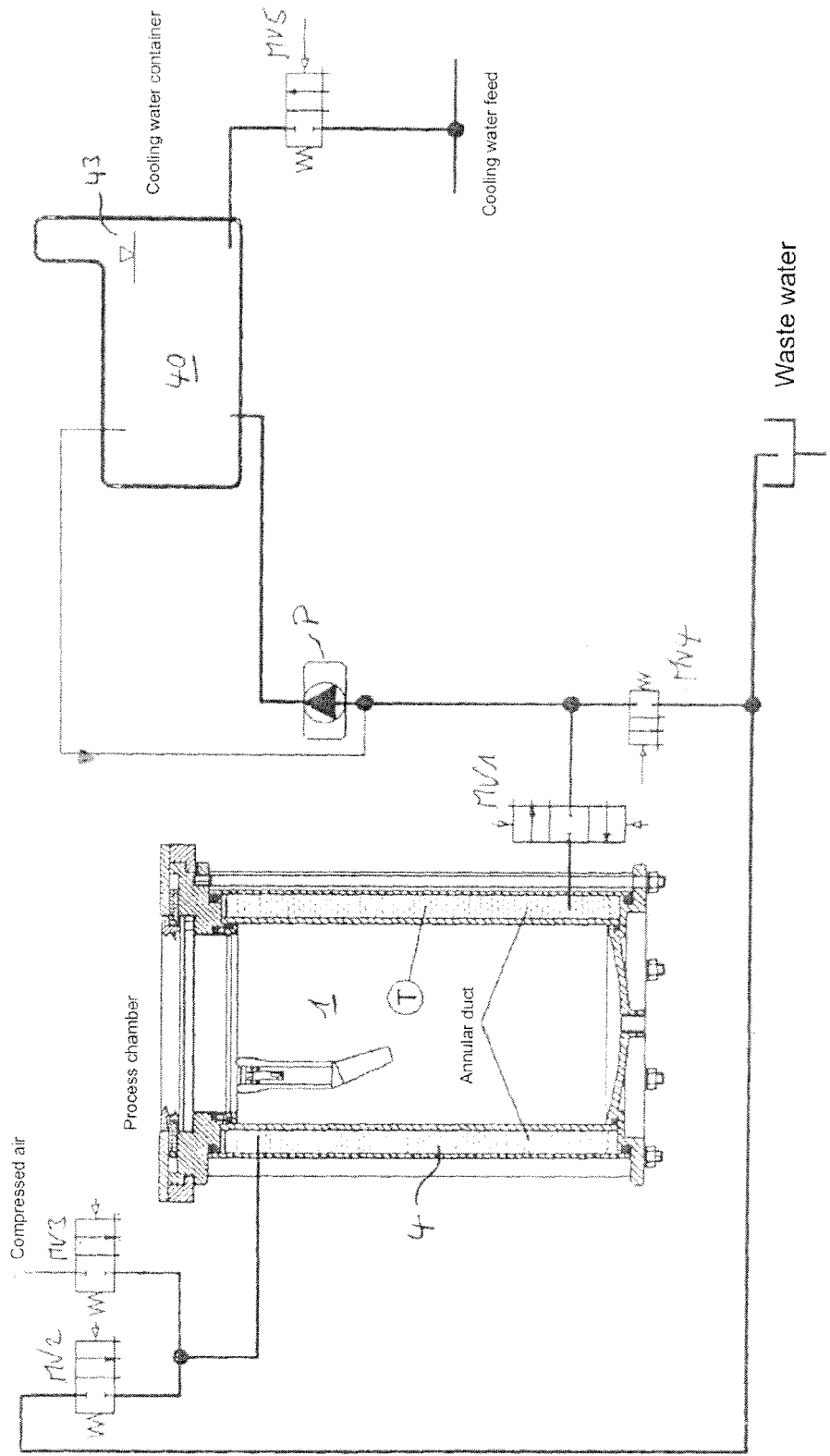

DEVICE AND METHOD FOR DISINFECTING, STERILIZING AND/OR LOOKING AFTER MEDICAL, IN PARTICULAR DENTAL, INSTRUMENTS

BACKGROUND OF THE INVENTION

1. Field of the Invention

The present invention relates to a device and method for disinfecting, sterilizing and/or conditioning medical, in particular dental, instruments.

2. Related Technology

German Patent Specification DE 40 24 171 C2 describes a method and a maintenance station for disinfecting and conditioning medical, in particular dental, instruments. Here, the instruments are attached to holders provided for that purpose in a rinsing chamber. At the start of the disinfecting and conditioning operations, the instruments are initially subjected to internal and external cleaning by blowing them out in a water bath. After that, the rinsing chamber is filled afresh with water—but this time hot water—the water being heated up still further in the rinsing chamber. As a result, the instruments are boiled in the water bath. In the next step, the instruments are then subjected to internal drying and conditioning, for which purpose they are blown out with hot air, oil being blown into the instruments by means of the hot air. In order then to remove surplus oil, on the one hand, hot air is blown into the interior of the instruments at elevated pressure and, on the other hand, hot water with a surfactant additive is poured in and then pumped out again after a sufficient period of time. In German Patent DE 40 24 171 C2, external drying takes place as a result of the instruments' own heat. Cold air is then additionally blown into the rinsing chamber for cooling purposes.

European Patent Specification EP 0 638 297 B1 indicates a method which is similar to that in German Patent DE 40 24 171 C2 but which, in addition to the cold cleaning, hot cleaning and maintenance of the instruments with oil, also carries out sterilization of the instruments afterwards from the inside and also from the outside. For this purpose, use is made of saturated water vapor at, preferably, 134° C. and a pressure of 2 to 2.5 bar. Here too, the drying and cooling of the instruments again takes place by blowing in cold air.

In the known methods and devices which have been described above, the amount of time consumed for drying and cooling the instruments is not inconsiderable. This comes about, among other things, through the fact that the instruments on the one hand have a high degree of moisture after disinfection or sterilization and, on the other hand, are intensively heated in the course of disinfection or sterilization. Thus an intensive [and] drying and cooling phase is needed after the disinfection/sterilization.

SUMMARY OF THE INVENTION

The invention provides devices for disinfecting, sterilizing and/or conditioning medical, in particular dental, instruments, with a view to markedly accelerating and improving the drying and cooling of the instruments and thus guaranteeing that they can be re-used more quickly.

Accordingly, the invention provides a device for disinfecting, sterilizing and/or conditioning medical, in particular dental, instruments, the device having:

a rinsing chamber;

holders located in the rinsing chamber for receiving the instruments; and a compressed air and water supply system;

characterized in that at least parts of the walls of the rinsing chamber or elements located inside the rinsing chamber can be cooled.

Further, the invention provides a method for disinfecting, sterilizing and/or conditioning medical, in particular dental, instruments, in which the instruments are located in the rinsing chamber of a device, characterized in that at least parts of the walls of the rinsing chamber or elements located inside the rinsing chamber are cooled, at least during a cooling or drying phase.

According to the invention, provision is now made for a device having a compressed air and water supply system for disinfecting, sterilizing and/or conditioning medical, in particular dental, instruments to have a rinsing chamber with holders for receiving the instruments, wherein the walls of the rinsing chamber, or elements located therein, can be at least partially cooled.

For this purpose, the rinsing chamber may have, for example, a cavity in its outer wall which can be filled with coolant, for example water or glycol, and/or air, or else cooling elements in its walls.

In order to form the cavity in the rinsing chamber, two externally ribbed, annular containers may be inserted in one another, thereby producing, between the two outer walls of the containers, a cavity which contains the cooling ribs of the inner container.

With the aid of this device, it is now possible to accelerate markedly the cooling or drying of the instruments. For this purpose, at least part of the walls is cooled during the cooling or drying phase.

As an alternative to the form of embodiment previously described, a cooling coil could be arranged inside the rinsing chamber, which coil can be filled with air or a coolant, for example water or glycol, as desired. In this case, moreover, a heating coil is also preferably arranged inside the rinsing chamber, particularly in the bottom region of the latter. Under these circumstances, the cooling coil and, optionally, the heating coil may be separated from an inner region of the rinsing chamber by a partition which has a number of apertures or openings and forms a guard against contact. This partition may be formed, in particular, by an inner container which is detachably connected to an outer container forming the rinsing chamber.

It is now possible to pump cold coolant continuously into the cavity or cooling coil via a coolant connection during the cooling and drying phase, while at the same time the same quantity of heated coolant leaves the cavity or coil via one of two outlets. During the disinfecting, sterilizing or conditioning phase, on the other hand, the cavity is exclusively filled with air. In particular, the cavity or the cooling coil may be a constituent part of a closed cooling circuit, the cooling circuit having a coolant reservoir and also means, in particular a fan and/or cooler, for cooling the coolant leaving the cavity or cooling coil. As an alternative to this closed circuit, however, control means for feeding in the coolant could be provided that are constructed for the purpose of feeding coolant to the cavity or coil in a cooling or drying phase only when the temperature of the coolant located in the cavity or coil has exceeded a limiting temperature.

Instead of the cavity, cooling elements may also be used for cooling the walls of the rinsing chamber.

As a result of the cooling operation, water vapor on the walls of the rinsing chamber now condenses to form water and collects in the underside of the chamber. This water can then run away through the closable aperture on the underside of the rinsing chamber.

As a result of the cooling of the walls of the rinsing chamber, the air in the chamber is also cooled. This produces a slight vacuum in the rinsing chamber, as a result of which the boiling point of the water is lowered and the drying operation is accelerated still further.

In addition, the cooling operation is also further aided by the fact that air is blown into the rinsing chamber via a bacteria filter.

BRIEF DESCRIPTION OF THE DRAWINGS

The invention will be explained in greater detail below with the aid of the accompanying drawings, in which:

FIG. 1 shows a diagrammatic representation of a device according to the invention in side view;

FIG. 2 shows a diagrammatic representation of the device according to the invention shown in FIG. 1, at the intersecting edge A-A;

FIG. 6 shows a second variant for cooling the rinsing container by means of water.

DETAILED DESCRIPTION

Figure 4:
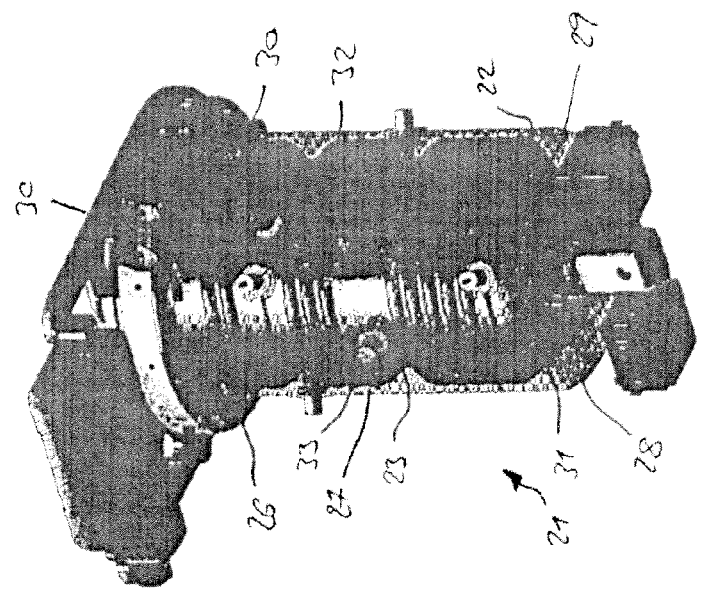
FIG. 4 shows a perspective view of the second exemplified embodiment.

The precise sequence of the drying and cooling phase according to the invention will be explained in greater detail below with the aid of the two drawings. The disinfecting, sterilizing and conditioning phase will not be gone into more precisely here, as their sequence is unimportant for the present invention and is already known from the prior art. All that is shown in the drawings, therefore, are those features which are of importance for a possible form of embodiment of the invention. The connections which are needed for the disinfecting, sterilizing or conditioning operation are accordingly not represented in FIGS. 1 and 2.

The device 1 shows a possible form of embodiment of the invention. In this connection, it has a rinsing chamber 3 in which instruments 2 are located, for disinfection, sterilization and maintenance, on holders which are provided for this purpose but are not shown any more precisely.

The rinsing chamber 3 is composed of two annular containers 10 and 11 which are inserted in one another in an extrusion press, a cavity 4 being produced between the outer container 10 and the inner container 11. The two containers 10 and 11 each have externally located cooling ribs 12. The cooling ribs 12 of the inner container 11 are accordingly located inside the cavity 4. In addition, the containers 10 and 11 are also configured in such a way that the cavity 4 is closed off in a sealing manner in the downward direction.

Now the cavity 4 has a compressed air connection 8, two water outlets 6 and 7 and a water connection 5, which are attached to the outer container 10 in each case. In addition, the rinsing chamber 3 also has a closable aperture 9 and a superheated steam inlet 13, both of which are attached, in the present form of embodiment, to the inner container 11.

The rinsing chamber 3, too, has a compressed air connection 15, this inlet 15 being provided with a bacteria filter 14.

One possible form of embodiment of the method according to the invention will now be gone into more precisely below. As already explained above, the disinfecting, sterilizing and conditioning phases will not be gone into more precisely, although it should be observed that, during these phases, the cavity 4 described above is filled with air, thereby producing a heat-insulating layer which leads to a reduction in the energy consumption needed for heating the water and water vapor.

After, for example, the sterilizing phase, in which superheated steam at over 130° has been conducted into the rinsing chamber via the superheated steam inlet 13, has been terminated, cold water is conducted into the cavity 4 via the water connection 5. This cools the rinsing chamber 3, as a result of which the interior space of the rinsing chamber 3 and the instruments 2 located therein also begin to cool rapidly. During this phase, cold water is continuously introduced into the cavity 4 via the water connection 5, under which circumstances the same quantity of heated water is discharged via the water outlet 7. By this means, it is constantly ensured that cold water is always located inside the cavity 4 and thus continuous cooling of the walls of the rinsing chamber 3 takes place.

As a result of the cooling of the rinsing chamber 3, the water vapor still located in the rinsing chamber 3 from the sterilizing operation condenses on the inner wall of the inner container 11 to form water. The water produced by condensation on the cooled inner walls of the inner container 11 then flows to the bottom of the rinsing chamber 3, where the closable aperture 9 is located. When this aperture 9 is open, the water is then able to leave the rinsing chamber 3. In addition, when the aperture 9 is closed, a slight vacuum is also produced because of the cooling of the air in the rinsing chamber 3, as a result of which the boiling point of the water is lowered and it is thus possible to accelerate and intensify the drying operation still further.

After the instruments 2 are sufficiently dry, the cooling phase follows, with cold water continuing to be pumped into the cavity 4 during this phase too. In addition, however, cool air is still conducted into the interior space of the rinsing chamber 3 via the compressed air inlet 15 and the bacteria filter 14, in order to aid the cooling of the instruments 2. As a result, the air located in the rinsing chamber 3 is set in motion, so that the heat of the instruments can be quickly transported away. The aim of this phase is to cool the instruments 2 to the point where it is possible for a user of the device 1 according to the invention to remove these from the rinsing chamber 3 safely.

Following the cooling phase, the water connection 5 and the water outlet 7 are then closed, the water outlet 6 is opened and compressed air is conducted into the cavity 4 through the compressed air inlet 8, as a result of which the cooling water is forced out of the cavity 4. As a result, the cavity 4 is then filled exclusively with air again, whereby the device 1 according to the invention is available for further disinfecting, sterilizing or conditioning phases with other instruments.

The drying operation is now accelerated through the fact that the water vapor is extracted from the interior space of the rinsing chamber 3 in an efficient and rapid manner as a result of the sudden cooling of the walls of the rinsing chamber 3. In the process, the water vapor located in the instruments, in particular, is also quickly extracted from the latter. In addition, the drying operation is also further accelerated through the fact that, when the aperture 9 is closed, a slight vacuum is produced in the rinsing chamber 3 because of the cooling of the air, as a result of which the boiling point of the water is lowered.

The cooling of the instruments is likewise made considerably shorter, on the one hand, by the cold water flowing through the cavity 4 and, on the other hand, by the cold air which is introduced.

The exemplified embodiment of the present invention shown in FIGS. 1 and 2 is merely one possible variant. The rinsing chamber could also, for example, equally well consist of a double-walled container.

A further form of embodiment of a corresponding process chamber or rinsing container which has been optimized for the purpose of reducing the cycle times for the warming-up and cooling-down phases will be explained below with the aid of FIGS. 3 and 4.

For this purpose, the rinsing chamber, which is designated generally by the reference symbol 21, is built up from a deep-drawn outer container 22, which is designed as a pressure vessel, and a deep-drawn, thin-walled inner container 23. Alternatively, the two containers 22 and 23 may also be designed as a welded structure consisting of a number of parts. Here, the outer container 22 is screwed to the container collar 25 via screw connections 24. A seal 26 in the form of a circumferential sealing ring is constructed between the outer container 22 and the container collar 25.

The inner container 23 is suspended from the container collar 25 and can easily be taken off in the upward direction for cleaning the rinsing chamber or replacing the heating system. Under these circumstances, the position of the inner container 23 is determined via pins constructed on the container collar 25 and corresponding clearances on the inner container 23. This ensures that the inner container 23 is correctly positioned with respect to the apertures for the cleaning nozzles for cleaning the instruments—which instruments are not represented.

Located in the intervening space between the outer container 22 and inner container 23 are a cooling coil 27 and also a heating coil 28. Since—as will be explained again in greater detail below—the inner container 23 is not sealed off in relation to the outer container 22, the cooling coil 27 and heating coil 28 are located with their entire area inside the rinsing chamber, as a result of which optimal transmission of heat or temperature coupling is guaranteed. In the exemplified embodiment represented, the surface of the cooling coil 27 amounts to about 2.5 times the cylindrical outer superficies. A very large area is therefore available for the transmission of heat. The cooling coil 27 is screwed to the outer container 22 by means of soldered-on or welded-on adapters 29. Welding or soldering to the outer container, such as would be necessary in the case of an externally located cooling coil, is not necessary in this solution. Alternatively, the heating coil 28, which is arranged on the underside of the inner container 23 in the exemplified embodiment represented, could also be attached to the bottom internally or externally as a sheet-type heating element.

In order to achieve an effective circulation of vapor between the outer container 22, or more precisely between the intervening space between the inner and outer containers, and the inner region of the inner container 23, openings or through-apertures 30 are provided in the upper region of the inner container 23. Other such openings are located in the region of the cleaning nozzles and also at the bottom. This bottom perforation 31 at the same time possesses a screening function, in order to prevent small parts from getting into the outlet of the container.

Temperature sensors 32 are also arranged on the outer face of the inner container 23. These are of angled design and are protected from mechanical damage by reason of their arrangement.

The cleaning nozzles 33 are screwed to the outer container 22 via a seal and direct a spray onto the instruments via a suitable aperture on the inner container 23. The fastening regions of the various screwing-on points are stamped, flat faces in each case and can easily be sealed off from the particular component, for example via O-rings, flat seals, etc. The heating coil 28 at the bottom of the container possesses a smaller external diameter than the internal diameter of the cooling coil 27 and can accordingly be removed or detached if necessary, without demounting the cooling coil 27. It might also optionally be possible to dispense with the inner container, which primarily represents a guard against contact.

Figure 3:
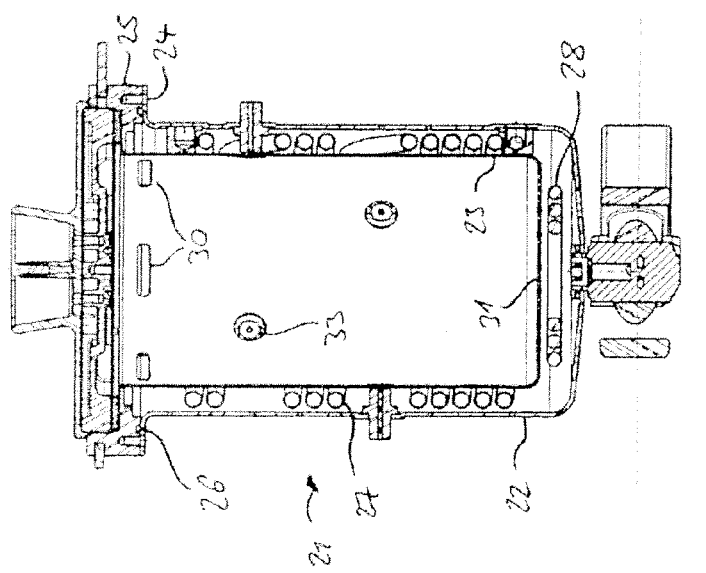
FIG. 3 shows the sectional representation of a second exemplified embodiment of a device according to the invention.

In the case of the rinsing chamber according to FIGS. 3 and 4, the cleaning of the instruments takes place in a manner comparable to that in the first exemplified embodiment. Initially, water for cleaning, rinsing-off and also sterilizing purposes is introduced into the chamber and heated up or vaporized via the heating system at the bottom of the container. The cleaning water is conducted, via the outlet valve located at the bottom of the container, to a circulating pump and is sprayed onto, or conducted through, the instruments via the nozzles in the container wall. Rinsing-off takes place in a similar manner.

Sterilizing water is then vaporized via the bottom heating system and heated up to 134° to 138° C. Under these circumstances, the superheated steam penetrates through all the cavities inside the chamber. For the final drying of the instruments and for cooling them, water is conducted through the cooling coil. The water vapor condenses on the cold cooling coil, this vapor being capable of easily flowing on, from the centre of the container, through the holes in the inner container, to the outer wall or cooling coil. In this case, too, rapid and effective cooling and drying of the instruments takes place because of the effects previously described.

In both the exemplified embodiments previously described, therefore, effective cooling of the rinsing chamber and of the goods to be rinsed located therein, is obtained through the fact that either the container or a cooling coil located therein has cold water or a coolant rinsing around it or rinsing through it. If water is used as the coolant, this should preferably be demineralized in order to avoid the deposition of lime and other water constituents on the hot container wall or cooling coil. Because of the costs resulting therefrom, the consumption of fresh water should accordingly be reduced as far as possible, for which reason the use of the cooling water preferably takes place in accordance with one of the two exemplified embodiments described below.

In this connection, a first variant is based on the use of the cooling water in a closed circuit and the return via an integrated cooler. In a second variant, too, the cooling water is taken from a storage tank. In this case, however, cooling takes place as a result of a through-flow with fresh cooling water which takes place at intervals or is slow and which is adapted to the transmission of heat. The two variants will be explained in more detailed form below with the aid of FIGS. 5 and 6, for which purpose a double-walled cooling chamber, such as is used in FIGS. 1 and 2, is represented. Naturally, however, the system could also be used in a rinsing chamber according to FIGS. 3 and 4 with an internally located cooling coil.

Figure 5:
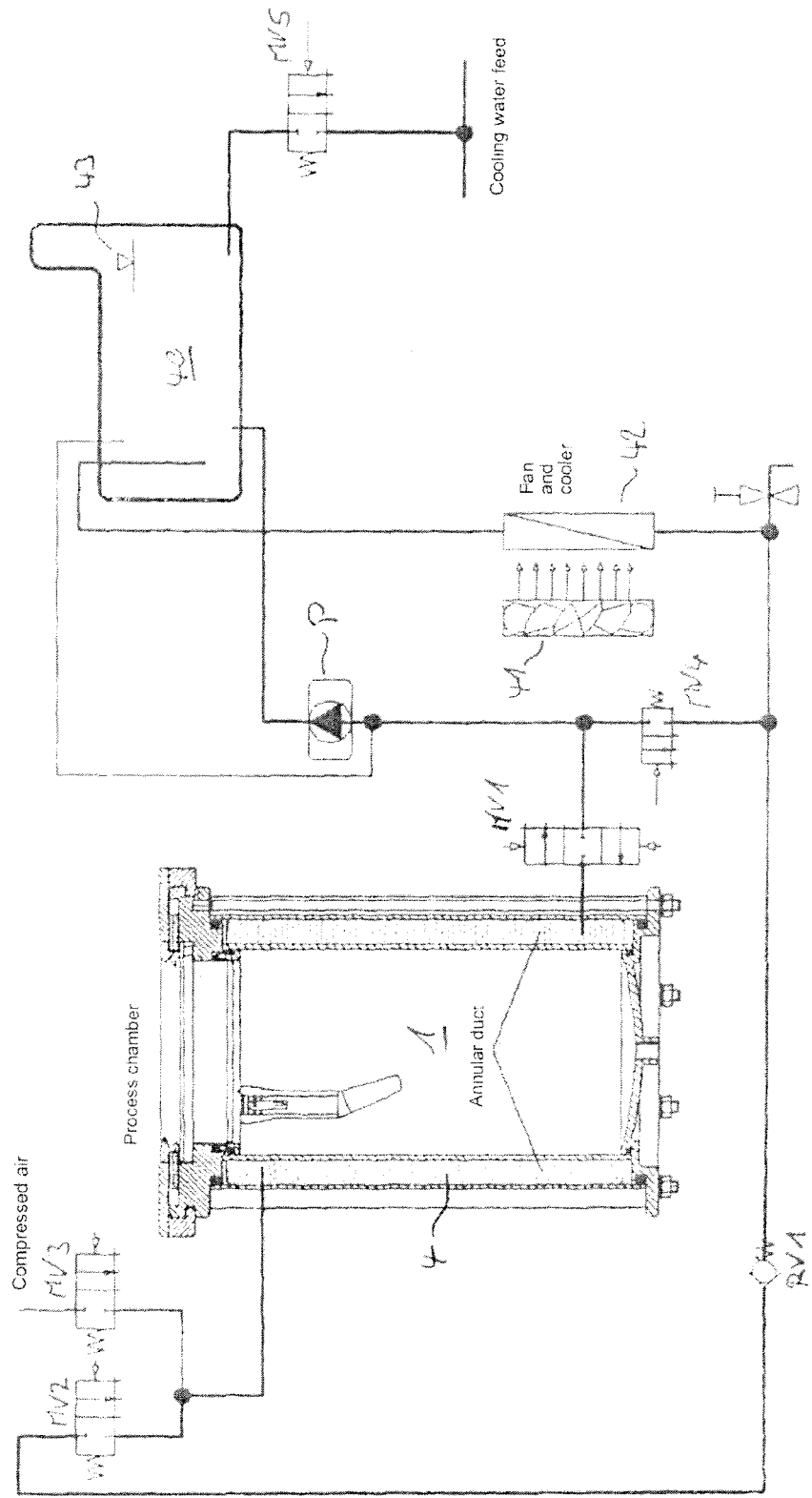
FIG. 5 shows a first variant for cooling the rinsing container by means of water.

In the variant according to FIG. 5, provision is made for the annular duct 4 of the rinsing chamber 3, which duct is located between the outer and inner walls of the container, to be empty during the sterilizing operation, the consequence of which—as previously explained—is that, above all, the inner wall of the chamber is heated. After the sterilizing operation has been completed, water is then pumped out of a cooling water container 40 and into the annular duct 4 via a first valve MV1—usually a magnetic valve—and a pump P. When the annular duct 4 is full, the water flows back into the cooling water container 40 via an outlet valve MV2 and also a non-return valve RV1, having been cooled beforehand with the aid of a fan 41 and/or cooler 42. The water fed back into the cooling water container 40 in this way can then be introduced into the cooling circuit again.

As a result of the combination represented, which consists of the fan 41/cooler 42 and water reservoir of the cooling water container 40, the cooling water can be kept at temperatures with the aid of which effective cooling of the rinsing chamber 3 is obtained. When the desired cooling temperature inside the rinsing chamber 3 is finally achieved, there is fed into the system, by opening a valve MV3, compressed air which forces the cooling water in the direction of the fan 41/cooler 42 and also the cooling water container 40 via the valve MV1 and also a further valve MV4, as a result of which the water is removed from the circuit. Renewed sterilization or preparation of the instruments can then be carried out.

Should the cooling water temperature inside the cooling water container 40 exceed a predetermined temperature value, circulation of the water via the pump P and the cooler/fan combination 41, 42 can be carried out via suitable activation of the valves MV1 and MV4, in order to briefly cool the water inside the cooling water container 40 with the valve MV1 closed. In the exemplified embodiment represented, losses of cooling water by evaporation are compensated for via the valve MV5. Under these circumstances, cooling water is, if necessary, topped up until a corresponding level switch 43 inside the cooling water container 40 responds.

The rinsing chamber 3 can therefore be effectively cooled with the aid of the cooling water circuit represented in FIG. 5, the losses of cooling water or consumption of cooling water being kept very low. This variant might accordingly also be used if another coolant, for example glycol, is used instead of water. Since, however, this variant is associated with a relatively high outlay, use may also be made, as an alternative to this, of an interval system as is represented in FIG. 6, in which identical elements have been provided with the same reference symbols.

In this case too, the annular duct 4 is initially empty during the sterilizing operation. After this sterilizing operation has been completed, water is pumped out of the cooling water container 40 and into the cooling duct 4 again via the valve MV1 the pump P. In this case, the filling volume is time-controlled via the pump P, surplus water being conducted away into the waste water via the valve MV2. The maximum filling level accordingly corresponds to the height of the annular duct 4.

When the annular duct 4 is full, the water initially remains in it until it is established, via a temperature sensor T, in conjunction with evaluating electronics, that effective cooling is no longer being obtained. In this case, cold water is then supplied via the valve MV1, and the heated cooling water leaves the annular duct 4 via the valve MV2 in the direction of the waste water. This operation is repeated until the predetermined temperature inside the rinsing chamber 3 is reached. Compressed air is then fed into the annular duct 4 to the cooling water by opening the valve MV3, so that this water passes into the waste water via the valves MV1 and MV4. The annular duct 4 is then once again devoid of cooling water and the rinsing chamber 3 is ready for a new sterilizing operation.

In this case too, the quantity of cooling water consumed is reduced, since new cooling water is only fed in afterwards when the temperature of the cooling water fed in hitherto has risen to the point where cooling of the rinsing chamber 3 is no longer obtained.

Both the variants in FIGS. 5 and 6 thus make it possible, when cooling the rinsing chamber by feeding in cooling fluid, to keep the need for cooling fluid at a low level.

In another possible form of embodiment for the process container, a hollow chamber or cooling coil is completely dispensed with. In this instance, however, cooling elements are then located in the walls of the rinsing chamber. In this case likewise, rapid cooling of the walls of the rinsing chamber is guaranteed, as a result of which the effects described in detail in the case of the form of embodiment having the hollow chamber likewise come into action and thereby also contribute to a markedly shortened drying and cooling phase.

The invention claimed is:

1. A device for disinfecting, sterilizing and/or conditioning instruments, the device comprising:
    a rinsing chamber;
    at least one instrument holder protruding inside the rinsing chamber, the at least one instrument holder connecting a dental instrument to an inner surface of the rinsing chamber;
    a heating element for producing steam;
    a steam inlet for conducting steam into the rinsing chamber; and
    a compressed air and water supply system;
    wherein at least parts of the walls of the rinsing chamber or elements located inside the rinsing chamber are cooled by cooling fluid, and the walls of the rinsing chamber have cooling elements for cooling purposes.

2. The device according to claim 1, wherein the rinsing chamber has a closable aperture on its underside.

3. The device according to claim 1, wherein the rinsing chamber has a compressed air connection that is provided with a bacteria filter.

4. The device according to claim 1, comprising an additional oil supply system.

5. The device according to claim 1, wherein the at least one instrument holder is configured to blow at least one of air, oil, and water into the dental instrument.

6. The device according to claim 1, wherein the heating element is configured to produce superheated steam.

7. A device for disinfecting, sterilizing and/or conditioning instruments, the device comprising:
    a rinsing chamber;
    at least one instrument holder protruding inside the rinsing chamber, the at least one instrument holder connecting a dental instrument to an inner surface of the rinsing chamber;
    a heating element for producing steam;
    a steam inlet for conducting steam into the rinsing chamber;
    a compressed air and water supply system; and
    a cooling coil that extends inside the rinsing chamber and is filled with air or a coolant,
    wherein at least parts of the walls of the rinsing chamber or elements located inside the rinsing chamber are cooled by the air or coolant.

8. The device according to claim 7, wherein the heating element comprises a heating coil arranged inside the rinsing chamber.

9. The device according to claim 8, wherein the heating coil is arranged in a bottom region of the rinsing chamber.

10. The device according to claim 8, wherein the heating coil is separated from an inner region of the rinsing chamber by a partition having a number of apertures or openings.

11. The device according to claim 10, wherein the partition is formed by an inner container that is detachably connected to an outer container forming the rinsing chamber.

12. The device according to claim 7, wherein the cooling coil is separated from an inner region of the rinsing chamber by a partition having a number of apertures or openings.

13. The device according to claim 12, wherein the partition is formed by an inner container that is detachably connected to an outer container forming the rinsing chamber.

14. The device according to claim 7, wherein the cooling coil is a constituent part of a closed cooling circuit, the closed cooling circuit having a means for cooling the coolant leaving the cooling coil.

15. The device according to claim 7, wherein the cooling coil is a constituent part of a cooling circuit which has a coolant reservoir, there being also provided control means for feeding in the coolant which is constructed for the purpose of feeding coolant to the cooling coil in a cooling or drying phase only when the temperature of the coolant located in the cooling coil has exceeded a limit temperature.

* * * * *